United States Patent [19]

Yabuuchi et al.

[11] 4,322,425
[45] Mar. 30, 1982

[54] COMPOSITIONS FOR TREATING GLAUCOMA

[75] Inventors: Yoichi Yabuuchi; Shiro Yoshizaki; Kazuyuki Nakagawa, all of Tokushima, Japan

[73] Assignee: Otsuka Pharmaceutical Co., Ltd., Tokyo, Japan

[21] Appl. No.: 191,245

[22] PCT Filed: Jul. 13, 1979

[86] PCT No.: PCT/JP79/00185
§ 371 Date: Mar. 14, 1980
§ 102(e) Date: Mar. 14, 1980

[87] PCT Pub. No.: WO80/00215
PCT Pub. Date: Feb. 21, 1980

[51] Int. Cl.$^3$ .......................................... A61K 31/47
[52] U.S. Cl. ................................................. 424/258
[58] Field of Search ....................................... 424/258

[56] References Cited
U.S. PATENT DOCUMENTS

| 4,022,776 | 5/1977 | Nakagawa et al. | 424/258 |
| 4,022,784 | 5/1977 | Nakagawa et al. | 424/258 |
| 4,026,897 | 5/1977 | Nakagawa et al. | 424/258 |
| 4,068,076 | 1/1978 | Nakagawa et al. | 424/258 |
| 4,072,683 | 2/1978 | Nakagawa et al. | 424/258 |
| 4,223,137 | 9/1980 | Yoshizaki et al. | 424/258 |

OTHER PUBLICATIONS

Chem. Abst. 93, 137,996(u), (1980)–Yabuuchi et al.
Chem. Abst. 91, 204,340(z), (1979)–Saito et al.

Primary Examiner—Douglas W. Robinson
Attorney, Agent, or Firm—Armstrong, Nikaido, Marmelstein & Kubovcik

[57] ABSTRACT

A glaucoma treating composition and method of treating glaucoma by administering the glaucoma treating composition to a patient are provided. The glaucoma treating composition comprises a carbostyril derivative, or acid addition salt thereof, having an intraocular pressure reducing activity in combination with an ophthalmically acceptable carrier, the barbostyril derivative being represented by the formula:

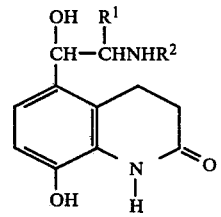

wherein $R^1$ and $R^2$ are each lower alkyl, and the carbon-to-carbon bond between the 3-position and the 4-position of the carbostyril skeleton is a single bond or double bond.

6 Claims, No Drawings

COMPOSITIONS FOR TREATING GLAUCOMA

TECHNICAL FIELD

This invention relates to compositions for treating glaucoma.

BACKGROUND ART

Glaucoma is attributable basically to a sustained or repeated increase in the intraocular pressure and causes functional and further organic disorders to the eye. For the treatment of this disease, it is considered to be a matter of urgency to reduce the increased intraocular pressure to the normal level to maintain the proper visual function (Masakichi Mikuni and Kazuo Iwata, "Glaucoma," Kanehara Shuppan Co., Ltd., 1968).

DISCLOSURE OF INVENTION

The glaucoma treating compositions of this invention comprise, as the active component thereof, a carbostyril derivative represented by the formula

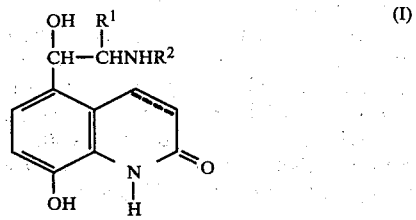

wherein $R^1$ and $R^2$ are each lower alkyl, and the carbon-to-carbon bond between the 3-position and the 4-position of the carbostyril skeleton is a single bond or double bond, or an acid addition salt thereof.

The lower alkyl groups represented by $R^1$ and $R^2$ in the formula (I) are straight-chain or branched-chain alkyl groups having 1 to 4 carbon atoms, such as methyl, ethyl, propyl, isopropyl, butyl, tert-butyl, etc. Useful acid addition salts of the carbostyril derivatives represented by the formula (I) are acid addition salts thereof which are usually pharmaceutically acceptable and which include, for example, salts of hydrochloric acid, sulfuric acid, nitric acid, hydrobromic acid, oxalic acid, maleic acid, fumaric acid, citric acid, tartaric acid, etc.

Given below are typical examples of the active compounds represented by the formula (I) and useful for the glaucoma treating compositions of this invention.

8-Hydroxy-5-(1-hydroxy-2-isopropylaminobutyl)carbostyril

8-Hydroxy-5-(1-hydroxy-2-tert-butylaminopropyl)carbostyril

8-Hydroxy-5-(1-hydroxy-2-ethylaminobutyl)-3,4-dihydrocarbostyril

8-Hydroxy-5-(1-hydroxy-2-isopropylaminobutyl)-3,4-dihydrocarbostyril

The compounds represented by the formula (I) and useful as the active components are known compounds prepared, for example, by the process disclosed in Published Examined Japanese Patent Application No. 10994/1978. The active compounds have bronchodialatory activity and useful for curing bronchial asthma.

This invention has been accomplished based on the finding that a group of carbostyril derivatives known as agents for treating bronchial asthma include compounds which are capable of exhibiting an efficacy as glaucoma treating agents, namely, an intraocular pressure reducing effect which is irrelevant to, and totally unexpected from, the efficacy as the bronchial asthma treating agent.

The glaucoma treating compositions of this invention can be formulated as suitable dosage unit forms by admixing a derivative of the formula (I) or an acid addition salt thereof with a usual carrier for ophthalmic preparations. The compositions can be in the form of any various usual dosage unit forms including ophthalmic ointments, ophthalmic solutions, etc. for local administration, and tablets, granules and injection solutions, etc. for general administration. It is especially preferable to use the compositions of this invention in the form of ophthalmic solutions.

Although the dosage of the present treating compositions is not particularly limited, the compositions are usually given at a daily dose of 0.01 to 0.5 mg, preferably 0.05 to 0.1 mg, for the adult, calculated as the active component of the compositions. Preferably the compositions are administered in two to three divided daily doses. It is usually preferable that the content of the active component contained in the compositions range from about 0.04 to about 2% by weight.

The treating compositions of this invention can be prepared in the usual manner with use of the derivative of the formula (I) or an acid addition salt thereof as the active component, by admixing the active component with a suitable carrier or excipient and, if required, formulating the mixture into the desired dosage unit form. The compositions, when formulated in the form of ophthalmic ointments, ophthalmic solutions or injection solutions, are further subjected to sterilization. Suitable carriers or diluents are selected for use in accordance with the form of the compositions. Examples of carriers useful for the preparation of ophthalmic ointments are emulsifiable carriers, water-soluble carriers and suspendable carriers. Typical of such carriers are white vaseline, purified lanolin, liquid paraffin, etc. Typical of diluents for preparing ophthalmic solutions is sterile distilled water.

Solubilizing agents, stabilizers, buffers, antioxidants, preservatives, etc. can further be incorporated into the compositions of this invention. Examples of useful solubilizing agents are sodium carboxymethyl cellulose; polyoxyethylene ethers such as polyoxyethylene lauryl ether and polyoxyethylene oleyl ether; higher fatty acid esters of polyethylene glycol such as polyethylene glycol monolaurate and polyethylene glycol monooleate; fatty acid ester of polyoxyethylene such as polyoxyethylene sorbitan monolaurate and polyoxyethylene sorbitan monooleate; etc. Examples of useful stabilizers are hydroxypropylmethyl cellulose, polyvinyl alcohol, carboxymethyl cellulose, hydroxyethyl cellulose, glycerin, EDTA, etc. Examples of useful buffers are sodium hydrogenphosphate, potassium hydrogenphosphate, boric acid, sodium borate, citric acid, sodium citrate, tartaric acid, sodium tartrate, etc. Examples of useful antioxidants are sodium bisulfite, sodium thiosulfite, ascorbic acid, etc. Examples of useful preservatives are chlorobutanol, benzalkonium chloride, cetylpyridinium chloride, phynylmercury salt, thimerosal, phenethyl alcohol, methylparaben, propylparaben, etc.

The compositions of this invention, when in the form of ophthalmic solutions, should preferably be made isotonic with tears. For this purpose, common salt or the like can be added to the compositions as desired. It is desirable to adjust the pH of the ophthalmic solutions to 5.5 to 8.5, preferably 6.5 to 7.5.

The glaucoma treating compositions of this invention thus prepared are given to patients by various methods in accordance with the form of the preparations. Ophthalmic solutions are applied dropwise to the eye from a suitable container or sprayed onto the eye from an applicator. Ophthalmic ointments are also applied to the eye. Tablets and granules are orally given, while injection solutions are administered subcutaneously, intramuscularly or intravenously. The desired therapeutic effect can be achieved in any of these cases.

The invention will be described below in greater detail with reference to preparation examples and medicinal efficacy test, to which the invention is not limited.

| Preparation Example 1 | |
| --- | --- |
| 8-Hydroxy-5-(1-hydroxy-2-isopropyl-aminobutyl)carbostyril hydrochloride | 0.2 g |
| Benzalkonium chloride | 0.01 g |
| Sodium dihydrogenphosphate | 0.56 g |
| Potassium dihydrogenphosphate | 0.8 g |
| Distilled water | Suitable amount |
| Total | 100 ml |

The ingredients are dissolved in distilled water, and the solution is sterilized by filtering with suitable filter paper to formulate a glaucoma treating composition of this invention in the form of an ophthalmic solution.

| Preparation Example 2 | |
| --- | --- |
| 8-Hydroxy-5-(1-hydroxy-2-isopropyl-aminobutyl-3,4-dihydrocarbostyril hydrochloride | 0.2 g |
| Benzalkonium chloride | 0.01 g |
| Sodium dihydrogenphosphate | 0.56 g |
| Potassium dihydrogenphosphate | 0.8 g |
| Distilled water | Suitable amount |
| Total | 100 ml |

The ingredients are dissolved in distilled water, and the solution is sterilized by filtering with suitable filter paper to formulate a glaucoma treating composition of this invention in the form of an ophthalmic solution.

Efficacy test

A drop (about 25 μl) of the ophthalmic solution obtained in Preparation Example 1 is given twice a day, in the morning and evening, for three days to each of the eyes of three male patients with open angle glaucoma. The intraocular pressure of the eye is measured between 10 a.m. and 11 a.m. by Goldmann applanation tonometer. Table 1 shows the results.

TABLE 1

| Patient | | Intraocular pressure (mm Hg) | | | |
| --- | --- | --- | --- | --- | --- |
| | | Before application | 1 day later | 2 days later | 3 days later |
| A | L.E.* | 31.64 | 21.35 | 13.46 | 18.58 |
| | R.E.** | 25.32 | 17.42 | 14.75 | 15.67 |
| B | L.E. | 38.85 | 23.78 | 24.52 | 21.27 |
| | R.E. | 35.43 | 21.47 | 23.38 | 20.69 |
| C | L.E. | 23.57 | 18.68 | 14.75 | 16.37 |
| | R.E. | 26.17 | 17.95 | 15.74 | 14.65 |

*Left eye
**Right eye

Table 1 reveals that the glaucoma treating composition of this invention greatly reduces the intraocular pressure of the patients with glaucoma and produces an outstanding therapeutic effect.

The glaucoma treating composition obtained in Preparation Example 2 according to this invention is tested for efficacy in the same manner as above. The composition produces substantially the same effect of reducing the intraocular pressure.

We claim:

1. A method for treating glaucoma comprising administering to a patient a glaucoma treating composition comprising an intraoccular pressure reducing effective amount of a carbostyril derivative, or an acid addition salt thereof, in combination with a carrier suitable for ophthalmic preparations, said carbostyril derivative being represented by the formula:

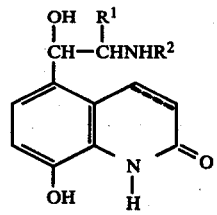

wherein $R^1$ and $R^2$ are each lower alkyl, and the carbon-to-carbon bond between the 3-position and the 4-position of the carbostyril skeleton is a single or double bond.

2. A method according to claim 1 wherein the composition is administered at a daily dose of 0.01 to 0.5 mg calculated as the active component.

3. A method according to claim 1 wherein the composition is administered at a daily dose of 0.05 to 0.1 mg calculated as the active component.

4. A method according to any one of claims 1-3, wherein the carbostyril derivative is a 8-hydroxy-5-(1-hydroxy-2-isopropylaminobutyl)carbostyril hydrochloride.

5. A method according to claim 4 wherein the composition is in the form of an ophthalmic solution which is isotonic with tears and has a pH of 5.5 to 8.5.

6. A method according to claim 1 wherein the glaucoma treating composition comprises from about 0.04 to about 2% by weight of the carbostyril derivative.

* * * * *